United States Patent
Bae et al.

(10) Patent No.: US 8,172,925 B2
(45) Date of Patent: May 8, 2012

(54) MULTI-FUNCTIONAL CABIN AIR FILTER

(75) Inventors: Gwi-Nam Bae, Seoul (KR); Seung Bok Lee, Chuncheon-si (KR); Jong Soo Jurng, Seoul (KR); Kil Choo Moon, Seoul (KR); Jae Soo Rhee, Bucheon-si (KR); Sang Woo Yom, Seongnam-si (KR); Kil Hong Song, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 388 days.

(21) Appl. No.: 12/607,120

(22) Filed: Oct. 28, 2009

(65) Prior Publication Data

US 2010/0296966 A1    Nov. 25, 2010

(30) Foreign Application Priority Data

May 19, 2009 (KR) .......................... 10-2009-0043582

(51) Int. Cl.
  B01D 53/56    (2006.01)
  B01D 53/72    (2006.01)

(52) U.S. Cl. ............... 95/129; 95/141; 95/285; 95/287; 96/55; 96/134; 96/226; 423/239.1; 55/385.3; 55/524

(58) Field of Classification Search ............... 96/15, 55, 96/108, 134, 154; 95/129, 141, 143, 285, 95/287; 423/239.1; 422/4, 122; 55/385.3, 55/524
See application file for complete search history.

(56) References Cited

U.S. PATENT DOCUMENTS

| 4,530,817 | A | * | 7/1985 | Holter et al. | ................. 422/122 |
| 4,551,304 | A | * | 11/1985 | Holter et al. | ....................... 422/4 |
| 5,486,410 | A | * | 1/1996 | Groeger et al. | ................ 442/353 |
| 6,068,824 | A | * | 5/2000 | Kinoshita et al. | .......... 423/239.1 |
| 6,773,477 | B2 | * | 8/2004 | Lindsay | ....................... 55/385.3 |
| 7,744,681 | B2 | * | 6/2010 | Marcoon | .......................... 95/285 |
| 7,749,312 | B2 | * | 7/2010 | Takigawa et al. | ................. 96/11 |

FOREIGN PATENT DOCUMENTS

KR    1020050086038 A    8/2005

OTHER PUBLICATIONS

Lee, Byung UK et al. "Inactivation of *S. epidermides*, *B. subtilis* and *E. coli* Bacteria Bioaerosols Deposited on a Filter Utilizing Airborne Silver Nanoparticles", J. Microbiol. Biotechnol. 2008, 18(1), 176-182.
Jun Ho Ji et al. "Evaluation of a Silver Nanoparticle Generator Using a Small Ceramic Heater for Inactivation of *S. epidermidis* Bioaerosols", Aerosol Science and Technology, 2007, 41: 786-793.

* cited by examiner

*Primary Examiner* — Frank Lawrence, Jr.
(74) *Attorney, Agent, or Firm* — Ohlandt, Greeley, Ruggiero & Perle LLP

(57) ABSTRACT

A multi-functional cabin air filter includes a dust collecting filter layer for collecting fine dust; an oxidation catalyst filter layer for oxidizing nitrogen monoxide into nitrogen dioxide; and an adsorption filter layer for adsorbing nitrogen dioxide and volatile organic compounds, wherein antimicrobial nanoparticles are applied to at least one of the dust collecting filter layer, the oxidation catalyst filter layer and the adsorption filter layer. This cabin air filter has dust collecting, denitrifying, deodorizing and antimicrobial functions, and it may be utilized in various ways for air purification in a limited space such as a vehicle.

9 Claims, 6 Drawing Sheets

MULTI-FUNCTIONAL CABIN AIR FILTER

CROSS-REFERENCE TO RELATED APPLICATION

This application claims under 35 U.S.C. §119 priority to and benefit of Korean Patent Application No. 2009-0043582, filed on May 19, 2009. Korean Patent Application No. 2009-0043582 is incorporated herein by reference in its entirety.

BACKGROUND

1. Field

This disclosure relates to a multi-functional cabin air filter utilizable in a limited space such as a vehicle.

2. Description of the Related Art

A vehicle has a general air filter with a dust collecting function, which is also called an air conditioner filter, and the air filter is inserted into an inlet of an air conditioner of the vehicle. However, in most cases, the air filter just has a dust collecting function, and it is not provided with a gaseous contaminant removing function or an antimicrobial function.

Recently, air conditioner filters having additional functions such as an antimicrobial or deodorizing function in addition to the dust collecting function have been released in the market. To remove gaseous air pollutants, an adsorbent such as activated carbon is used. In some products, a room-temperature catalyst filter is coupled to decompose and remove the adsorbed gaseous substances.

However, air pollutants contaminating the indoor of a vehicle include fine dust and nitrogen oxides emitted from a vehicle exhaust pipe to the road. Nitrogen oxides include nitrogen monoxide and nitrogen dioxide, and nitrogen monoxide occupies about 90% or more of the nitrogen oxides emitted from a vehicle. In the air, nitrogen monoxide is oxidized into nitrogen dioxide through atmospheric chemical reaction. Accordingly, in the vehicle indoor contaminated by high-concentration exhaust gas emitted from a vehicle, the concentration of nitrogen monoxide is higher than that of nitrogen dioxide. However, a general adsorbent such as activated carbon adsorbs a relatively small amount of nitrogen monoxide though its adsorbing performance for nitrogen dioxide is excellent. Thus, in order to efficiently remove nitrogen monoxide, another technique is required in addition to the adsorbent.

Also, in case a filter is provided with an antimicrobial function by applying a biodegradable antimicrobial agent such as chitosan to a dust collecting filter, the antimicrobial agent may be degraded with the lapse of use or storage time, thereby deteriorating the antimicrobial function. In addition, in case of an antimicrobial filter made by coating its surface with a liquid-phase inorganic antimicrobial agent such as silver, a large amount of antimicrobial agent is nonuniformly coated on the surface, which may result in inappropriate antimicrobial function or cause additional pressure drop across the filter.

SUMMARY

In one aspect, there is provided a multi-functional cabin air filter having dust collecting, denitrifying, deodorizing and antimicrobial functions.

In another aspect, there is provided an air purifying method using the multi-functional cabin air filter.

In one embodiment, there is provided a multi-functional cabin air filter, which includes a dust collecting filter layer for collecting fine dust; an oxidation catalyst filter layer for oxidizing nitrogen monoxide into nitrogen dioxide; and an adsorption filter layer for adsorbing nitrogen dioxide and volatile organic compounds, wherein antimicrobial nanoparticles are applied to at least one of the dust collecting filter layer, the oxidation catalyst filter layer and the adsorption filter layer. Also, there is provided an air purifying method using the above cabin air filter.

The above cabin air filter has dust collecting, denitrifying, deodorizing and antimicrobial functions, and it may be utilized in various ways for air purification in a limited space such as a vehicle.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION

Figure 1:
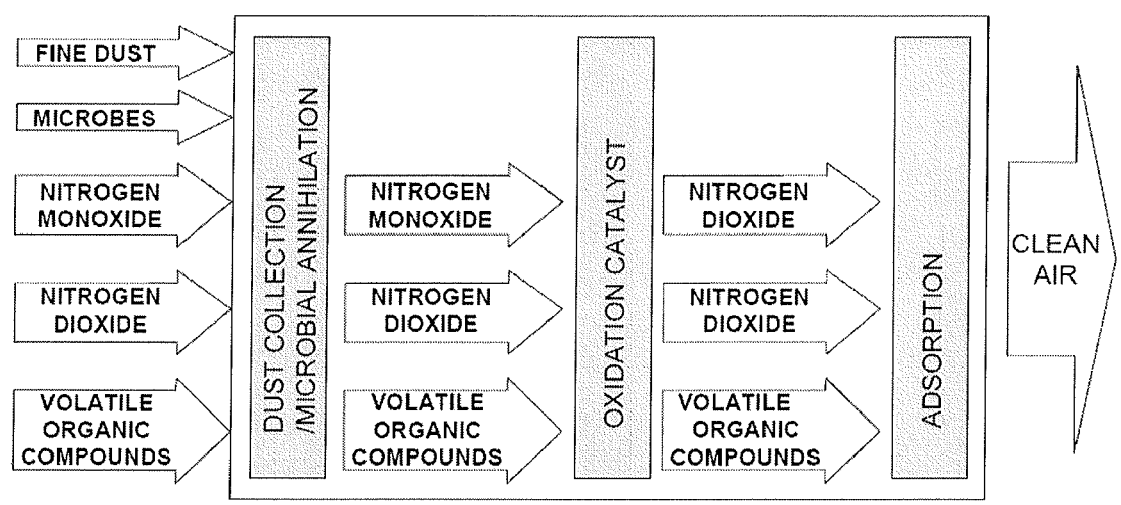
FIG. 1 is a conceptual view showing a cabin air filter according to one embodiment disclosed herein.

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. Furthermore, the use of the terms "a", "an", etc. does not denote a limitation of quantity, but rather denotes the presence of at least one of the referenced item. The use of the terms "first", "second", and the like does not imply any particular order, but they are included to identify individual elements. Moreover, the use of the terms "first", "second", etc. does not denote any order or importance, but rather the terms "first", "second", etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the drawings, like reference numerals in the drawings denote like elements. The shape, size and regions, and the like, of the drawing may be exaggerated for clarity.

A cabin air filter according to one embodiment disclosed herein is a multi-functional cabin air filter having dust collecting, denitrifying, deodorizing and antimicrobial functions. In more detail, the multi-functional cabin air filter includes: a dust collecting filter layer for collecting fine dust; an oxidation catalyst filter layer for oxidizing nitrogen monoxide into nitrogen dioxide; and an adsorption filter layer for adsorbing nitrogen dioxide and volatile organic compounds, wherein antimicrobial nanoparticles are applied to at least one of the dust collecting filter layer, the oxidation catalyst filter layer and the adsorption filter layer.

In one embodiment, the cabin air filter may be made by coupling a dust collecting filter, a catalyst and an adsorbent in order and then depositing them with antimicrobial metal nanoparticles. In more detail, a catalyst layer for oxidizing nitrogen monoxide into nitrogen dioxide is located at the downstream of the dust collecting filter layer, and an adsorbent for adsorbing nitrogen dioxide and volatile organic compounds is located at the downstream of the catalyst layer. In this arrangement, the layers are coupled. Then, antimicrobial metal nanoparticles prepared in a vapor phase are applied to the coupled cabin air filter unit such that the particles are deposited uniformly on a surface of the dust collecting filter layer, a surface of the catalyst filter layer, and a surface of the adsorption filter layer.

The dust collecting filter layer plays a role of filtering off fine dust. In one embodiment, the dust collecting filter may remove 99% or more of fine dust with a size of 5 μm (micrometers) or larger.

In one embodiment, at least one of the oxidation catalyst filter layer and the adsorption filter layer may have a honeycomb structure. By adopting the honeycomb structure, catalyst or activated carbon may not be inclined to one side in spite of impact or vibration, and it is possible to minimize the increase of pressure drop that may occur when relatively large amount of catalyst or activated carbon granules are needed to be filled to maintain the initial performance for a long time. In addition, large pellets and fibers coated with the catalyst or the activated carbon may also be used with no limitation.

In another embodiment, a separate dust collecting filter layer may be added at the downstream of the oxidation catalyst filter layer or the adsorption filter layer. It helps to intercept leakage of dust that may occur in the oxidation catalyst filter layer or the adsorption filter layer.

In one embodiment, the oxidation catalyst filter layer may include at least one oxidation catalyst selected from the group consisting of copper oxide (CuO), manganese dioxide ($MnO_2$) and dipotassium oxide ($K_2O$). In detail, the above three catalysts may be mixed at a suitable ratio, and in more detail, the catalyst may include 23% of CuO, 69% of $MnO_2$ and 4% of $K_2O$. The catalyst filled in the oxidation catalyst filter layer oxidizes nitrogen monoxide into nitrogen dioxide at a room temperature. Generally, activated carbon tends to adsorb a relatively small amount of nitrogen monoxide, so an adsorption efficiency may be greatly improved by oxidizing nitrogen monoxide into nitrogen dioxide and then adsorbing the nitrogen dioxide.

The adsorption filter layer may include activated carbon granules or activated carbon fibers. The activated carbon component may efficiently adsorb not only nitrogen dioxide but also volatile organic compounds (VOCs). The VOCs generally include gas-phase or liquid-phase organic compounds easily evaporated into the air due to high vapor pressure. Such VOCs are carcinogenic substances as well as air pollutants, and they are also considered as the cause agents of global warming. Examples of the VOCs include benzene, toluene, ethylbenzene, xylene and acetylene. After nitrogen monoxide is oxidized into nitrogen dioxide as it passes through the oxidation catalyst filter layer, the nitrogen dioxide is adsorbed by the activated carbon or activated carbon fiber.

In one embodiment, the antimicrobial filter layer may be configured by applying antimicrobial nanoparticles to at least one of the dust collecting filter layer, the oxidation catalyst filter layer and the adsorption filter layer. By applying antimicrobial nanoparticles on existing filter layers, it is possible to decrease the volume of the air filter unit, save the antimicrobial substances, and ensure more efficient antimicrobial effect. In another embodiment, the antimicrobial filter layer may be configured by applying antimicrobial nanoparticles to separate filter media. In case a biodegradable organic antimicrobial agent is applied to dust collecting media, the antimicrobial agent may be degraded with the lapse of use or storage time, thereby deteriorating the antimicrobial function. In addition, in case a liquid-phase antimicrobial agent is applied, additional pressure drop across the filter or nonuniformity of the applied antimicrobial agent may occur. In the embodiment disclosed herein, inorganic antimicrobial nanoparticles are used to solve the above problems.

In one embodiment, the antimicrobial nanoparticles may be at least one selected from the group consisting of silver (Ag), copper (Cu), zinc (Zn) and magnesium (Mg), and desirably silver nanoparticles may be used. The term 'nanoparticle' used herein generically refer to particles whose size is in the range of several nanometers to several hundred nanometers.

In one embodiment, the dust collecting filter layer of the air filter may include an electrostatic filter made by providing an electrostatic property to a filter media. The electrostatic filter is advantageous in that it may efficiently collect fine charged dust, which is not easily filtered through an existing dust collecting filter. The term 'electrostatic' used herein means that electric polarization persists for a long time although an external electric field is nonexistent, thereby forming an electric field at the surroundings. The electrostatic filter makes fine dust be electrically adhered to its filter media, so it exhibits an excellent dust collecting efficiency with low pressure drop.

As disclosed herein, there is also provided an air purifying method using the above cabin air filter. The air purifying method includes: a dust collecting process for collecting fine dust; an oxidation catalyst reaction process for oxidizing nitrogen monoxide into nitrogen dioxide; an adsorption process for adsorbing nitrogen dioxide and volatile organic compounds; and an antimicrobial process for preventing or inhibiting proliferation of microbes.

In the dust collecting process, fine dust is removed, and then the air free from fine dust is contacted with an oxidation catalyst to oxidize nitrogen monoxide into nitrogen dioxide. Also, an adsorbent is located at the downstream of the catalyst layer to adsorb nitrogen dioxide and volatile organic compounds. Finally, proliferation of microbes is controlled through the filter layer treated with antimicrobial agents. In one embodiment, the antimicrobial process may be executed subsequently after or together with any one of the dust collecting process, the oxidation process and the adsorption process.

Hereinafter, a cabin air filter according to one embodiment is explained in detail with reference to the accompanying drawings.

FIG. 1 is a conceptual view showing a cabin air filter. While an air introduced into the air filter passes through the dust collecting filter layer deposited with silver nanoparticles, fine dust is removed and microbes are annihilated. After that, while the air passes through the oxidation catalyst filter layer filled with catalyst, nitrogen monoxide is oxidized into nitrogen dioxide. Also, while the air passes through the adsorption filter layer, the nitrogen dioxide is removed together with volatile organic compounds. The dust collecting filter layer may adopt filter media capable of removing 99% or more of fine dust with a size of 5 μm (micrometers) or larger.

Figure 2:
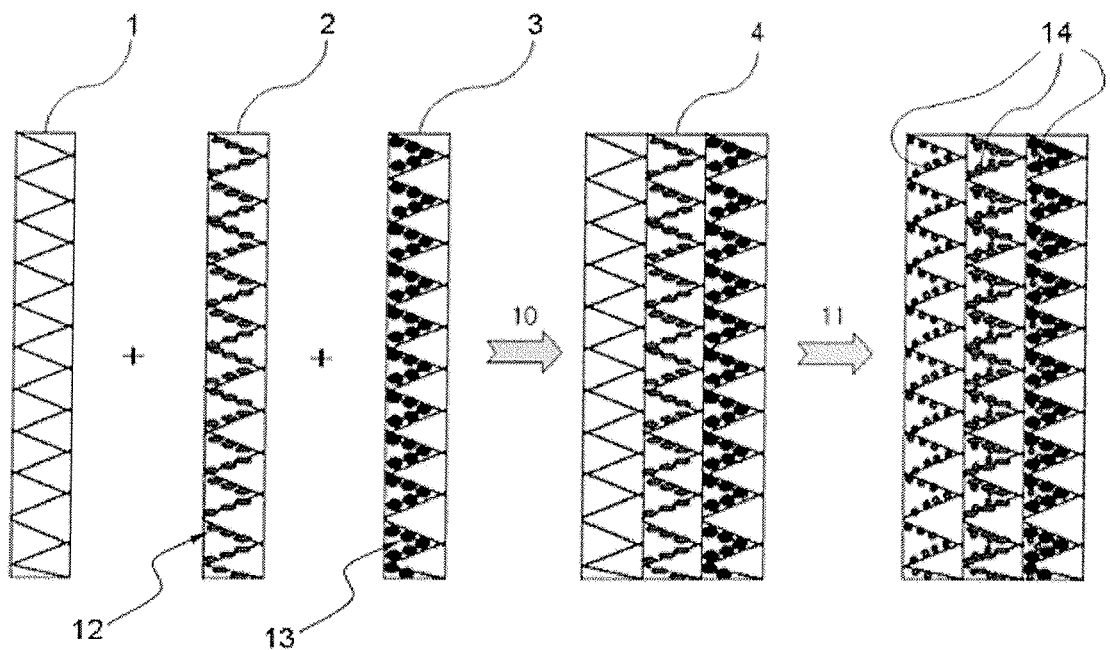
FIG. 2 is a sectional view illustrating an assembling process of the cabin air filter according to one embodiment.

FIG. 2 is a sectional view showing an assembling process of the cabin air filter according to one embodiment disclosed herein. Referring to FIG. 2, the cabin air filter is further provided with a denitrifying function and a deodorizing function through the step 10 of coupling a dust collecting filter layer 1, an oxidation catalyst filter layer 2 and an adsorption filter layer 3, in addition to a basic dust collecting function. The oxidation catalyst filter layer 2 is configured such that an oxidation catalyst 12 is filled between two filter media, and the adsorption filter layer 3 is configured such that small activated carbon granules 13 are filled between two filter media. Until then, the resultant product is a cabin air filter unit 4 without an antimicrobial function. If the cabin air filter unit 4 without an antimicrobial function is deposited with antimicrobial silver nanoparticles 14 prepared in a vapor phase, silver nanoparticles 14 are adhered not only to the dust collecting filter layer 1 but also to the oxidation catalyst filter layer 2 and the adsorption filter layer 3 at its downstream. The cabin air filter manufactured as mentioned above has dust collecting, denitrifying, deodorizing and antimicrobial functions. Also, even though a dust collecting filter that was pre-processed to have an antimicrobial function is used instead of a general dust collecting filter, the antimicrobial function may be reinforced through the above process.

Figure 3:
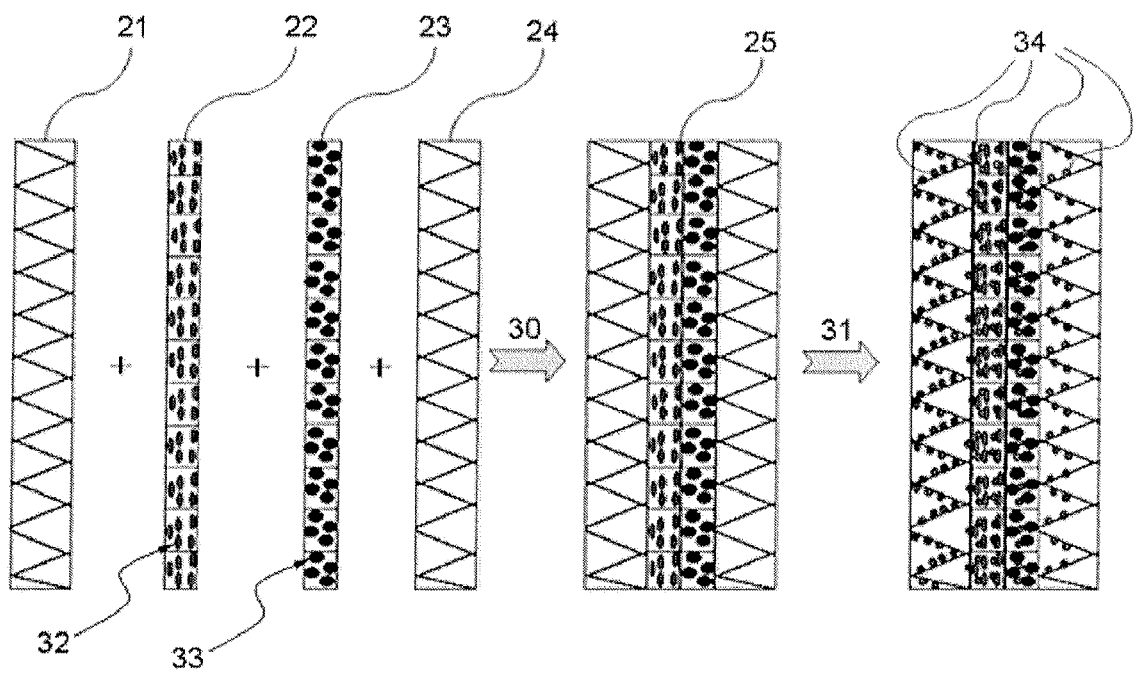
FIG. 3 is a sectional view showing an assembling process of the cabin air filter according to another embodiment.

FIG. 3 is a sectional view showing a cabin air filter according to another embodiment. Referring to FIG. 3, for manufacturing the cabin air filter of this embodiment, the step 30 of coupling a dust collecting filter layer 21, an oxidation catalyst filter layer 22, an adsorption filter layer 23 and a dust collecting filter layer 24 is executed to assemble a cabin air filter unit 25 having a denitrifying function and a deodorizing function in addition to a basic dust collecting function. If the cabin air filter unit 25 is deposited with antimicrobial silver nanoparticles 34 prepared in a vapor phase, the silver nanoparticles 34 are adhered not only to the dust collecting layers 21, 24 but also to the oxidation catalyst filter layer 22 and the adsorption filter layer 23. Also, the oxidation catalyst filter layer 22 and the adsorption filter layer 23 have a honeycomb structure. In more detail, the oxidation catalyst filter layer 22 and the adsorption filter layer 23 are respectively made by filling a catalyst 32 and activated carbon 33 to a case with a honeycomb structure. In this case, by adding the dust collecting filter 24 at the downstream of the adsorption filter with a honeycomb structure, dust that may be generated in the cabin air filter is not leaked out.

EXAMPLES

The examples and experiments will now be described. The following examples and experiments are for illustrative purposes only and not intended to limit the scope of this disclosure.

Experimental Example 1

Experiment for Measuring NO Oxidation Rate

The performance of catalyst used in the cabin air filter shown in FIG. 3 was tested. The used catalyst included 23 weight % of CuO, 69 weight % of $MnO_2$ and 4 weight % of $K_2O$. While injecting an air at a face velocity of 0.16 meters/sec (m/s), concentrations of NO and $NO_2$ were measured at the upstream and downstream of the catalyst layer, respectively. Also, at the point that 150 seconds passed from the measurement of concentration, NO gas was injected. The experimental results of NO and $NO_2$ concentrations are shown in FIG. 4.

Figure 4:
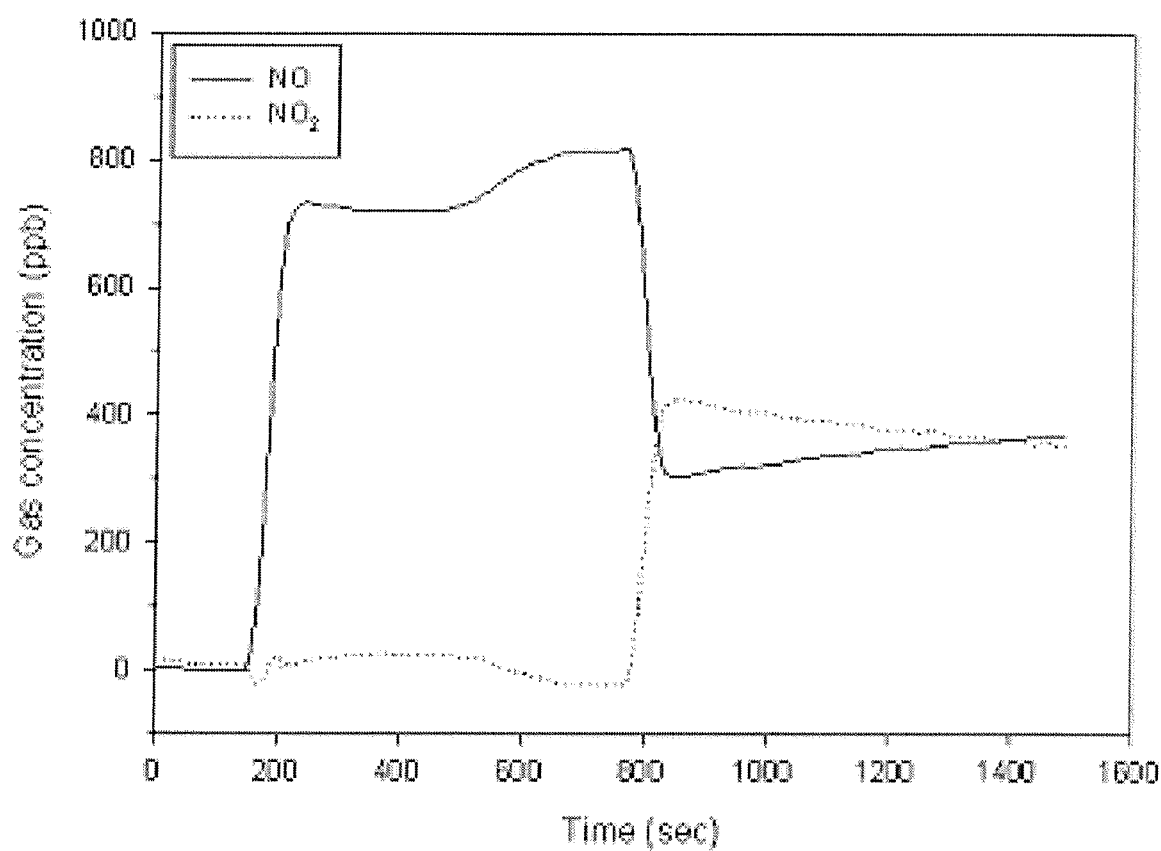
FIG. 4 is a graph showing an experimental result of NO oxidation of the cabin air filter.

Referring to FIG. 4, the concentration of NO measured at the upstream of the catalyst layer was 700~800 parts per billion (ppb). After about 760 seconds, the measurement position was changed from the upstream to the downstream of the catalyst layer. The concentration of NO was decreased to about 300~350 ppb at the downstream of the catalyst layer. Also, a concentration of $NO_2$ was increased as much as the decreased concentration of NO. In compliance with the experimental results, NO oxidation rate by the catalyst was about 60%.

Experimental Example 2

Experiment for Measuring Absorption Performance of Volatile Organic Compounds

For the cabin air filter shown in FIG. 3, adsorption performances of volatile organic compounds such as toluene, benzene, ethylbenzene and xylene were tested. In detail, when a test gas in which the concentration of toluene, benzene, ethylbenzene and meta (m-), para (p-) and ortho- (o-)xylene, respectively, was about 800 ppb passed at a face velocity of 0.8 m/s, those concentrations were measured at the upstream and downstream of the cabin air filter, respectively. The experimental results of adsorption efficiencies are shown in FIG. 5.

Figure 5:
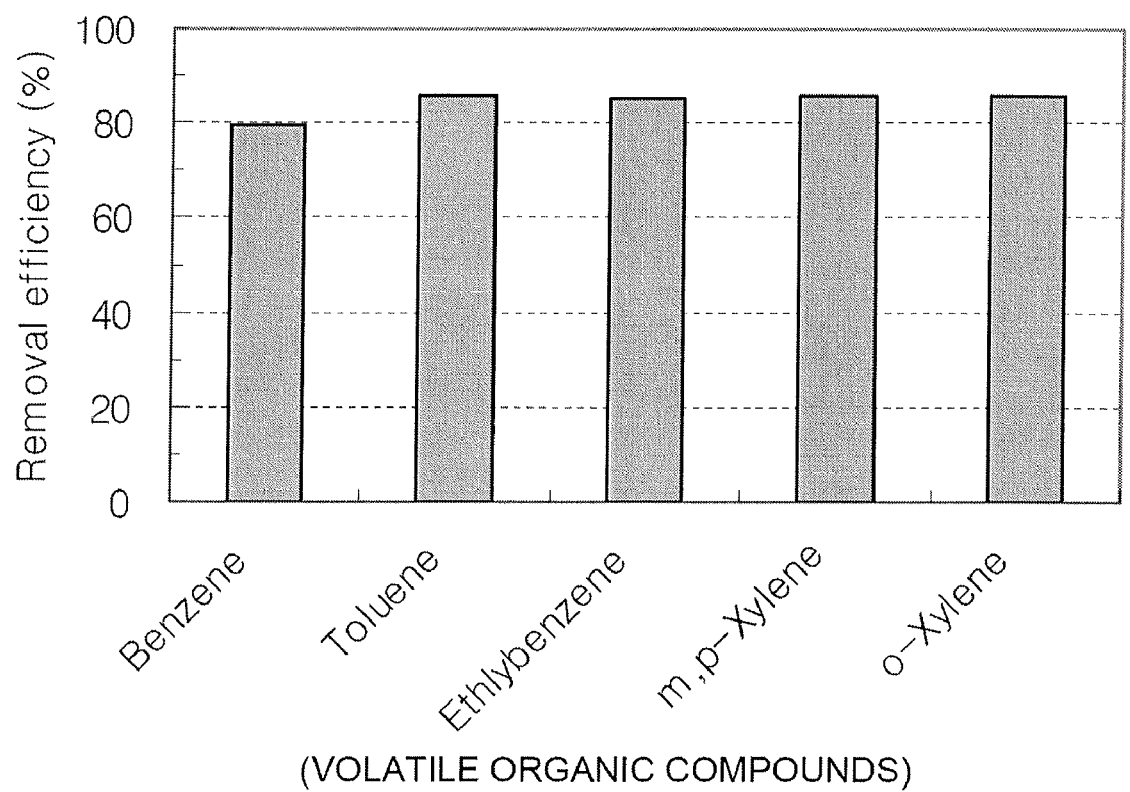
FIG. 5 is a graph showing an experimental result of adsorption of the cabin air filter for various volatile organic compounds.

Referring to FIG. 5, it would be understood that the cabin air filter disclosed herein removes toluene, benzene, ethylbenzene and xylene at an efficiency of 80 to 86%.

Experimental Example 3

Antimicrobial Test

For the dust collecting filter media, antimicrobial performances in case silver nanoparticles are applied and in case silver nanoparticles are not applied were measured and compared with each other. For this experiment, microbes were aerosolized into the air and collected on the surface of the dust collecting filter media, and then the dust collecting filter media was put into a liquid medium and shaken therein. After that, the dust collecting filter media was taken out of the liquid medium, and then microbes in the liquid medium were cultivated for 64 hours. During the cultivating process, an optical density of the liquid medium was measured with time to check whether the microbes were proliferated. The experimental results of optical density are shown in FIG. 6.

Figure 6:
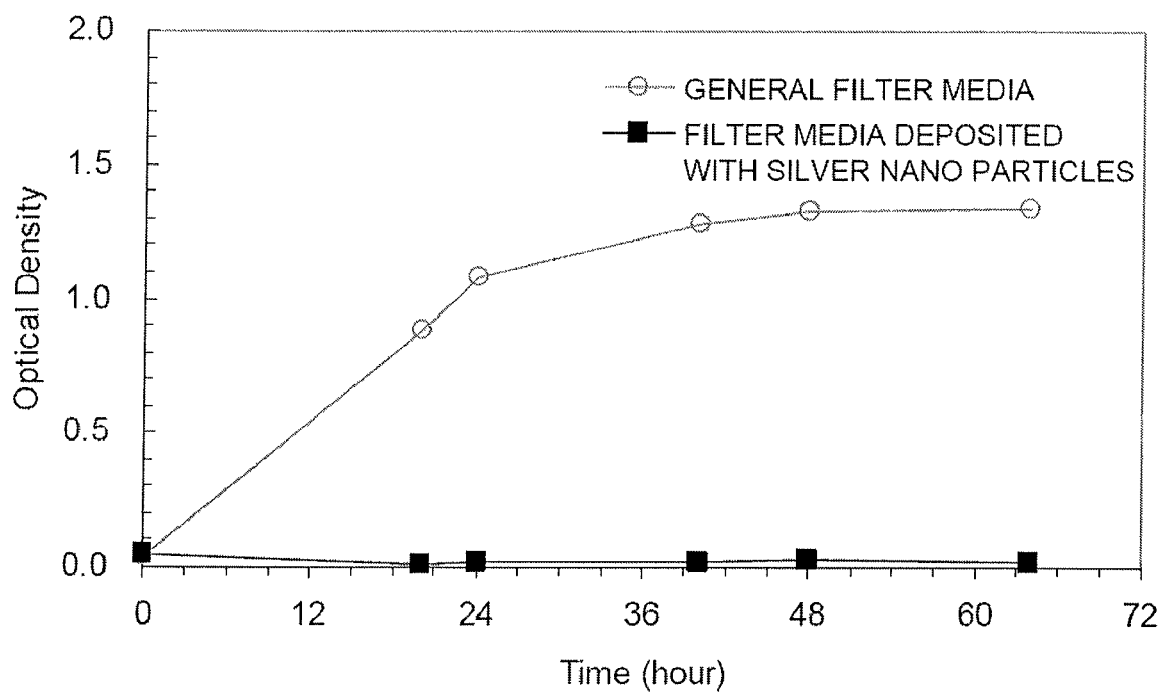
FIG. 6 is a graph showing an experimental result of antimicrobial performance of the cabin air filter.

Referring to FIG. 6, in case of general dust collecting filter media not deposited with silver nanoparticles, the optical density was obviously increased due to the proliferation of microbes. However, in case of dust collecting filter media deposited with silver nanoparticles, it was found that an optical density was not increased even after 64 hours since microbes were annihilated. Thus, it could be understood that the antimicrobial function is added by applying silver nanoparticles to the filter media.

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

What is claimed is:

1. A multi-functional cabin air filter, comprising:
   a dust collecting filter layer for collecting fine dust;
   an oxidation catalyst filter layer for oxidizing nitrogen monoxide into nitrogen dioxide; and
   an adsorption filter layer for adsorbing nitrogen dioxide and volatile organic compounds,
   wherein antimicrobial nanoparticles are applied to at least one of the dust collecting filter layer, the oxidation catalyst filter layer and the adsorption filter layer.

2. The multi-functional cabin air filter according to claim 1, wherein at least one of the oxidation catalyst filter layer and the adsorption filter layer has a honeycomb structure.

3. The multi-functional cabin air filter according to claim 2, wherein a separate dust collecting filter layer is added at a downstream of the oxidation catalyst filter layer or the adsorption filter layer.

4. The multi-functional cabin air filter according to claim 1, wherein the oxidation catalyst filter layer includes at least one oxidation catalyst selected from the group consisting of CuO, $MnO_2$ and $K_2O$.

5. The multi-functional cabin air filter according to claim 1, wherein the adsorption filter layer includes activated carbon granules, pellets, or fibers.

6. The multi-functional cabin air filter according to claim 1, wherein the antimicrobial nanoparticle is at least one selected from the group consisting of silver (Ag), copper (Cu), zinc (Zn) and magnesium (Mg).

7. The multi-functional cabin air filter according to claim 1, wherein the dust collecting filter layer further comprises a filter medium that is an electrostatic filter.

8. A method for purifying air introduced into a cabin air filter, comprising:
   collecting fine dust from the air with the cabin air filter;
   oxidizing nitrogen monoxide from the air into nitrogen dioxide with the filter;
   adsorbing nitrogen dioxide and volatile organic compounds from the air onto the filter; and
   preventing or inhibiting proliferation of microbes in the air with the filter.

9. The method of claim 8, wherein the step of preventing or inhibiting proliferation of microbes occurs simultaneously with at least one other step of claim 8.

* * * * *